United States Patent [19]

Erdman et al.

[11] Patent Number: 4,720,382
[45] Date of Patent: Jan. 19, 1988

[54] INHIBITING THE CORROSION OF HAIR CONDITIONING COMPOSITIONS

[75] Inventors: Constance E. Erdman; W. Stephen Tait, both of Racine County, Wis.

[73] Assignee: S. C. Johnson & Son, Inc., Racine, Wis.

[21] Appl. No.: 909,612

[22] Filed: Sep. 19, 1986

Related U.S. Application Data

[63] Continuation-in-part of Ser. No. 804,409, Dec. 4, 1985, abandoned.

[51] Int. Cl.$^4$ ................................................. A61K 7/06
[52] U.S. Cl. .......................................... 424/70; 424/78
[58] Field of Search ............................................. 424/70

[56] References Cited

U.S. PATENT DOCUMENTS

| | | | |
|---|---|---|---|
| 4,389,259 | 6/1983 | Danner et al. | 148/6.15 R |
| 4,421,740 | 12/1983 | Burton | 424/70 |
| 4,465,516 | 8/1984 | Danner et al. | 106/14.120 |

FOREIGN PATENT DOCUMENTS

| | | | |
|---|---|---|---|
| 56-16405 | 2/1981 | Japan | 424/70 |
| 0077217 | 6/1981 | Japan | 424/70 |
| 0077218 | 6/1981 | Japan | 424/70 |
| 0077614 | 5/1982 | Japan | 424/70 |

OTHER PUBLICATIONS

Harry's Cosmeticology, 6th Ed., pp. 434–435.
Sandocorin 8015 Liquid-Safety Data Sheet, Sandoz, 2 pages, 1982.
Advertisement entitled "Sandocorin . . . A New Approach to an Age-Old Problem—Corrosion", 1 page.
Sandocorin 8015 Liquid-Data Sheet No. 7154/83, Sandoz, 12 pages, 1983.
Sandocorin 8000 Liquid-Safety Data Sheet, Sandoz, 2 pages, 1979.
Sandocorin 8000 Liquid-Provisional Data Sheet, Sandoz, 1 page.

*Primary Examiner*—Dale R. Ore

[57] ABSTRACT

Asymmetrical diesters of orthophosphoric acid are added to corrosive hair conditioning compositions to inhibit corrosion of metal coming into contact with the composition. The hair conditioning properties of the hair conditioning compositions are not adversely affected.

16 Claims, No Drawings

INHIBITING THE CORROSION OF HAIR CONDITIONING COMPOSITIONS

BACKGROUND OF INVENTION

This application is a continuation-in-part of Ser. No. 804,409 which was filed on Dec. 4, 1985, now abandoned.

The present invention relates to a method of inhibiting the corrosion of a corrosive chloride or methosulfate ion-containing hair conditioning composition. In particular, an asymmetrical diester of orthophosphoric acid is added to a chloride or methosulfate ion-containing hair conditioning composition in amounts effective to inhibit corrosion of metal coming into contact with the composition. Additionally, the present invention relates to hair conditioning compositions containing corrosion inhibiting amounts of asymmetrical diesters of orthophosphoric acid.

Hair conditioning formulations, commonly referred to as creme rinses and hair conditioners, generally contain quaternary ammonium chloride and/or methosulfate conditioning agents, such as, stearyl dimethyl benzyl ammonium chloride, distearyldimonium chloride, dicetyldimonium chloride, behenyltrimethyl ammonium methosulfate and dipalmethyl hydroxy-ethylmonium methosulfate. Also, creme rinses and hair conditioners may contain conditioning amines which have been neutralized with hydrochloric acid (HCL), such as, for example, stearyl dimethyl amine or stearamidopropyl dimethylamine neutralized with HCL. The chloride ions of these hair conditioning systems are corrosive to metal substrates and, in particular, to stainless steel. Also, the methosulfate ion-containing compositions are corrosive. Since stainless steel is commonly used in the machinery employed by industry for producing, pumping, homogenizing and transferring hair conditioning compositions during the manufacturing and filling processes, the stainless steel is open to attack by these compositions which results in corrosion.

U.S. Pat. No. 4,389,259 and 4,465,516 disclose asymmetrical diesters of orthophosphoric acid useful as corrosion inhibitors in the presence of electrolytes. The asymmetrical diesters of orthophosphoric acid are preferably combined with heterocyclic compounds, such as, mercaptobenzothiazoles, benzotriazoles and sodium boroheptonate; pH-adjusting agents; biocides; anti-scaling agents; mild oxidizing agents; and surfactants. The corrosion inhibiting compositions described in U.S. Pat. No. 4,389,259 and 4,465,516 are disclosed as being useful corrosion inhibiting compositions for use in (1) aqueous systems such as domestic heating systems or (2) aqueous or water/glycol systems such as those used in internal combustion engines. The corrosion inhibiting compositions may also be added to liquid or foam type fire extinguishers and to wood pulp to inhibit corrosion of the metal parts in paper making machines.

In view of the above, it is readily apparent that it is desirable to inhibit the corrosion potential of chloride and methosulfate ion-containing creme rinse and hair conditioner compositions. Heretofore, asymmetrical diesters of orthophosphoric acid have not been disclosed as being useful corrosion inhibiting agents in cosmetic formulations such as creme rinses and hair conditioners.

Summary of Invention

Briefly, in accordance with the present invention, the corrosivity of chloride or methosulfate ion containing hair conditioning compositions is reduced by the addition of an effective corrosion inhibiting amount of an asymmetrical diester of orthophosphoric acid to the hair conditioning compositions. The corrosion inhibiting agent does not adversely affect the hair conditioning properties of the composition.

The present asymmetrical diesters of orthophosphoric acid are added to hair conditioning compositions during the manufacturing process to inhibit corrosion of the metal machinery and metal pipes in which the composition comes into contact with. The orthophosphoric acid diesters are added to the composition in amounts of at least about 25 parts per million (ppm) based on the total weight of the hair conditioning composition. The present diesters can also be added to intermediates which are corrosive to metal substrates if corrosive intermediates are prepared and then combined subsequently to form hair conditioning compositions.

Of particular interest in the practice of the present invention, SANDOCORIN 8000 orthophosphoric acid diester, commercially available from Sandoz Color and Chemicals, Specialties Chemical Department, Charlotte, N.C. 28205, is added to chloride or methosulfate ion containing creme rinses in amounts effective to reduce the corrosivity of the creme rinses. These improved creme rinses maintain their hair conditioning properties while at the same time have a reduced corrosion propensity to stainless steel.

DETAILED DESCRIPTION OF THE INVENTION

In the practice of the present invention it is essential to employ a corrosive chloride or methosulfate ion-containing hair conditioning composition and an asymmetrical diester of orthophosphoric acid. When used herein the term "hair conditioning composition" is meant to encompass hair conditioners and creme rinses.

The chloride or methosulfate ion containing hair conditioning compositions are any of the standard hair conditioning compositions containing a source of free chloride or methosulfate ions. Typically, the source of chloride ions is a quaternary ammonium chloride conditioning agent or a conditioning amine which has been neutralized with hydrochloric acid. The source of the methosulfate ion is a quaternary ammonium methosulfate conditioning agent.

Other ingredients can be included in the present hair conditioning compositions including polymeric setting agents and other cosmetic additives such as perfumes, dyes, herbs, thickening agents, preservatives, biocides and the like. All of these ingredients are well known to one skilled in the art and are employed in concentrations readily determinable by one skilled in the art. Hair conditioning compositions are described in detail in Harry's Cosmeticology, 6th Edition, U.S. Pat. No. 4,421,740 and the Chemistry and Manufacture of Cosmetics, Vol. 4, 2nd Edition all of which are incorporated herein by reference.

The asymmetrical diesters of orthophosphoric acid employed in the practice of the present invention are those diesters of the formula I below:

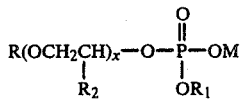

(FORMULA I)

wherein
R represents $C_1$–$C_{20}$ alkyl;
$R_1$ represents $C_1$–$C_{20}$ alkyl;
$R_2$ represents —H or —$CH_3$;
M represents hydrogen, an alkali metal ion or an equivalent of an alkaline earth metal ion or zinc ion; and
X represents 1–15.

Mixtures of compounds of Formula I can also be employed in practicing the present invention. These compounds are known compounds and are described in U.S. Pat. Nos. 4,389,259 and 4,465,516 which are incorporated herein by reference.

Preferred compounds of Formula I above include those wherein R represents $C_8$–$C_{18}$ alkyl, $R_1$ represents $C_1$–$C_5$ alkyl, $R_2$ represents hydrogen, x represents 3–12 inclusive, and M represents sodium, potassium, one half calcium or one half zinc. Especially preferred compounds of Formula I include those compounds wherein R represents $C_{12}$–$C_{16}$ alkyl, $R_1$ represents $C_2$–$C_4$ alkyl such as propyl, n-butyl or butyl, $R_2$ represents hydrogen, x represents 6–9 inclusive and M represents sodium, potassium or one half zinc.

The compounds of Formula I above are added to chloride or methosulfate ion-containing hair conditioning compositions in an amount of at least about 25 parts per million (ppm) based on the total weight of the hair conditioning composition. Preferably, the compound of Formula I is added in amounts of from about 125 ppm to about 2,500 ppm. The optimum concentration of the diester phosphate of Formula I above will depend upon a variety of factors, such as, for example, the particular hair conditioning composition employed and whether it is a finished product or a concentrated intermediate, the particular compound of Formula 1 employed, the metal substrate which will come into contact with the hair conditioning composition and physical parameters involved in the hair conditioning manufacturing process. i.e., temperature, pressure, humidity, etc. The optimum concentration of the asymmetrical diester of Formula I is readily determined by one skilled in the art by conducting routine electrochemical measurements.

The present diester compounds are added to the hair conditioning composition during the manufacturing process preferably before, or when, the chloride or methosulfate ion source is added into the formulation. The diester compounds can be added alone but are preferably added as aqueous concentrates containing up to 80% by weight of the diester compounds, preferably the corrosion inhibiting compounds of Formula I are added directly to the hair conditioning composition or the intermediate component of the hair conditioning composition which contains the chloride or methosulfate ion source.

Optionally, other ingredients can be present in the anti-corrosion concentrates. Suitable optional ingredients include heterocyclic compounds such as mercaptobenzothiazoles, benzotriazoles and sodium boroheptonate; pH adjusting agents; biocides; anti-scaling agents; surfactants; and mild oxidizing agents. These optional ingredients are, described in detail in the U.S. Pat. Nos. 4,389,259 and 4,465,516.

The hair conditioning compositions of the present invention can be the finished creme rinse or hair conditioner products or an intermediate employed in the manufacture of creme rinses and hair conditioners. Sometimes the final product will not be corrosive to some metals because the chloride or methosulfate ion concentration is insufficient to cause corrosion. Additionally, it is known that fragrances sometime inhibit corrosion. During the manufacturing process it is common to employ a hair conditioning intermediate which has high concentrations of the chloride or methosulfate ion source. Such hair conditioning intermediate compositions present a serious problem with regard to the corrosion of metal manufacturing equipment and in particular stainless steel. It is an important aspect of the present invention to prevent such intermediate compositions from causing corrosion to metal manufacturing equipment.

Hair conditioning intermediate compositions will contain the hair conditioning agent, i.e., quaternary ammonium chloride or methosulfate and/or a conditioning amine that has been neutralized with hydrochloric acid, and water. Optional ingredients include fatty alcohols and mineral oil. After the hair conditioning intermediate is prepared, it is admixed with a thickener intermediate to produce the final creme rinse composition. The thickener intermediate is an aqueous mixture containing water and a thickening agent and, optionally, standard cosmetic additives described herein such as protein, humectants, preservatives, biocides, dyes, herbs, fragrances and the like. The exact ratio of hair conditioning intermediate and thickener intermediate employed in preparing the finished hair conditioning composition product will depend upon the concentrations of ingredients in each. The intermediates will be admixed in amounts sufficient to form a finished hair conditioner or creme rinse having acceptable levels of all the ingredients.

In a preferred embodiment of the present invention, a creme rinse hair conditioning intermediate composition is prepared which contains the following ingredients:

| Ingredients | Range in Weight % |
| --- | --- |
| Hair conditioning agent | 2–4% |
| Orthophosphoric acid diester | 0.05–0.25% |
| Mineral Oil | 2–6% |
| Fatty alcohol | 2.5–7.5% |
| Water | Balance |

In preparing a creme rinse hair conditioning intermediate composition the water, fatty alcohol, diester and hair conditioning agents are charged to an appropriate vessel and heated with agitation to a temperature of between about 120° F. and about 150° F. The mineral oil is then added to the vessel and the mixture heated with agitation to a temperature of between about 160° F. and 180° F. The mixture is then allowed to cool to room temperature. The diesters of orthophosphoric acid are charged to the vessel before, or at, the time that the conditioning agent, i.e., chloride or methosulfate ion source, is charged in the vessel. The orthophosphoric acid diester is added to the intermediate mixture in amounts of at least about 25 ppm and preferably in amounts of from about 500–2,500 ppm.

When SANDOCORIN 8000 or 8015 is employed as the diester, it must be taken into account that SANDOCORIN is approximately 50% active ingredient. The SANDOCORIN 8000 composition is comprised of the following active ingredients: (a) CAS No. 64114-42-7, phosphoric acid, monobutyl ester, disodium salt, (b) CAS No. 73050-09-6, poly(oxy 1,2 ethanediyl), alpha-phosphono omega hydroxy-, $C_{13}$–$C_{15}$ alkyl ethers, disodium salts, (c) CAS No. 73050-08-5, poly(oxy 1,2 ethanediyl), alpha, alpha phosphinicobis (omega-hydroxy-, di-$C_{13}$–$C_{15}$ alkyl ethers, sodium salts, and (d) CAS No. 73050-07-4, poly(oxy 1,2 ethanediyl), alpha (butoxyhydroxy phosphinyl)-omega hydroxy-, $C_{13}$–$C_{15}$ alkyl ethers, sodium salts. The addition of the orthophosphoric acid diester will prevent corrosion to stainless steel manufacturing equipment which comes into contact with the intermediate composition. This intermediate composition can then be stored for future use or can be immediately admixed with a thickening intermediate to prepare a finished creme rinse product.

The following examples illustrate the practice of the present invention but should not be construed as limiting its scope.

EXAMPLE 1

Hair Conditioning Intermediate

The following ingredients were admixed according to procedures described below to prepare a hair conditioning Intermediate A containing a source of free chloride ions:

| INTERMEDIATE A | |
|---|---|
| INGREDIENTS | WEIGHT PERCENT |
| Steaylalkonium chloride | 2.3% |
| Amine chloride salt | 0.4% |
| Mineral oil | 4.0% |
| Fatty alcohol | 5.3% |
| Water | 88.0% |
| | 100.0% |

All of the above ingredient except the mineral oil were charged into a kettle and heated to 140° F. with agitation. The mineral oil was then added to the kettle and the mixture was heated to 170° F. with agitation for 30 minutes. The mixture was then allowed to cool to room temperature.

Intermediate A was tested by potentiodynamic scanning for corrosive potential on 316 and 316L stainless steel. The formula was found to be actively corrosive.

SANDOCORIN 8015 and 8000 were added to various samples of Intermediate A in amounts of 0.05, 0.1 and 0.25 percent by weight. These samples were tested for their corrosion behavior. All of the formulations containing SANDOCORIN 8015 and 8000 showed passive behavior. The hair conditioning properties of these treated samples were not adversely affected by the addition of the SANDOCORIN 8015 or 8000.

Intermediate A was formulated into a finished creme rinse by admixing 1 part by weight Intermediate A and 3 parts by weight aqueous thickener intermediate. The aqueous thickener intermediate contained a thickening agent in water and, optionally, protein, humectants, preservatives, biocides, dyes, herbs and fragrance. The thickener intermediate contained water in an amount of about 97% by weight.

EXAMPLE 2

Hair Conditioning Intermediate

Employing substantially the same procedures described in Example 1 the following ingredients were admixed to prepare a hair conditioning Intermediate B containing a source of methosulfate ions:

| INTERMEDIATE B | |
|---|---|
| INGREDIENTS | WEIGHT PERCENT |
| Behenyltrimethyl ammonium methosulfate | 2.5 |
| Mineral oil | 4.0 |
| Fatty alcohol | 4.8 |
| Water | 88.7 |

Intermediate B was tested by potentiodynamic scanning for corrosive potential on 316 and 316L stainless steel. The formula was found to be actively corrosive. Various samples of Intermediate B were tested for corrosion behavior after the addition of SANDOCORIN 8015 and 8000 in amounts of 0.05, 0.1 and 0.25 percent by weight. All showed passive behavior.

Intermediate B (1 part by weight) was admixed with the thickener intermediate (3 parts by weight) described in Example 1 to make a finished creme rinse product.

Similar results, i.e., corrosion inhibition, are achieved when the various compounds for Formula I are added to corrosive chloride or methosulfate ion containing hair conditioners, creme rinses and intermediates employed in their preparation.

We claim:

1. A method of inhibiting the corrosion to metal of a corrosive chloride or methosulfate ion-containing hair conditioning composition without adversely affecting the hair conditioning properties thereof which comprises adding to the chloride or methosulfate ion-containing hair conditioning composition an effective metal corrosion inhibiting amount of a compound of the formula

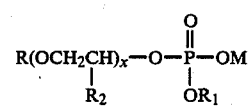

wherein
R represents $C_1$–$C_{20}$ alkyl;
$R_1$ represents $C_1$–$C_{20}$ alkyl;
$R_2$ represents —H or —$CH_3$;
M represents hydrogen, an alkali metal ion or an equivalent of an alkaline earth metal ion or zinc ion; and
X represents 1–15.

2. The method of claim 1 wherein R represents a $C_{12}$–$C_{16}$ alkyl, $R_1$ represents a $C_2$–$C_4$ alkyl, $R_2$ represents hydrogen, x represents 6–9 inclusive and M represents sodium, potassium or one half zinc.

3. The method of claim 2 wherein the corrosion inhibiting compound is added to the hair conditioning composition in an amount of at least about 25 ppm by weight.

4. The method of claim 3 wherein the corrosion inhibiting compound is added to the hair conditioning composition in an amount of from about 250 to about 2,500 ppm by weight.

5. The method of claim 4 wherein the corrosion inhibiting compound is added to the hair conditioning composition in an amount of from about 500–1,250 ppm by weight.

6. The method of claim 4 wherein the hair conditioning composition is a creme rinse intermediate.

7. The method of claim 2 wherein R represents $C_{13}$ alkyl or $C_{14}$ alkyl, $R_1$ represents n butyl, x represents 7 and M represents sodium.

8. A method of inhibiting the corrosion to metal of a corrosive chloride or methosulfate ion-containing hair conditioning composition without adversely affecting the hair conditioning properties thereof which comprises adding to the chloride or methosulfate ion-containing hair conditioning composition an effective metal corrosion inhibiting amount of a composition comprising the following active ingredients: (a) phosphoric acid, monobutyl ester, disodium salt, (b) poly(oxy-1,2-ethanediyl), alpha-phosphono-omega-hydroxy-, $C_{13}$–$C_{15}$ alkyl ethers, disodium salts, (c) poly(oxy-1,2-ethanediyl), alpha, alpha-phosphinicobis (omega-hydroxy, di–$C_{13}$–$C_{15}$ alkyl ethers, sodium salts, and (d) poly(oxy-1,2-ethanediyl), alpha-(butoxyhydroxyphosphinyl)- omega-hydroxy-, $C_{13}$–$C_{15}$ alkyl ethers, sodium salts.

9. In a corrosive hair conditioning composition which contains free chloride or methosulfate ions the improvement which comprises adding to the hair conditioning composition an effective corrosion inhibiting amount of a compound of the formula

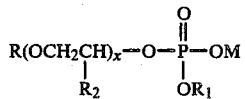

wherein
R represents $C_1$–$C_{20}$ alkyl;
$R_1$ represents $C_1$–$C_{20}$ alkyl;
$R_2$ represents —H or —$CH_3$;
M represents hydrogen, an alkali metal ion or an equivalent of an alkaline earth metal ion or zinc ion; and
X represents 1–15
whereby the improved hair conditioning composition is substantially non-corrosive to stainless steel and does not exhibit a loss in hair conditioning properties.

10. The improved composition of claim 9 wherein R represents $C_{12}$–$C_{16}$ alkyl, $R_1$ represents a $C_2$–$C_4$ alkyl, $R_2$ represents hydrogen, x represents 6–9 inclusive and M represents sodium, potassium or one half zinc.

11. The improved composition of claim 10 wherein the corrosion inhibiting compound is added to the hair conditioning composition in an amount of at least about 25 ppm by weight.

12. The improved composition of claim 11 wherein the corrosion inhibiting compound is added to the hair conditioning composition in an amount of from about 250 to about 2,500 ppm by weight.

13. The improved composition of claim 12 wherein the corrosion inhibiting compound is added to the hair conditioning composition in an amount of from about 500–1,250 ppm by weight.

14. The improved composition of claim 12 wherein the hair conditioning composition is a creme rinse intermediate.

15. The improved composition of claim 10 wherein R represents $C_{13}$ alkyl or $C_{14}$ alkyl, $R_1$ represents n-butyl, x represents 7 and M represents sodium.

16. In a corrosive hair conditioninq composition which contains free chloride or methosulfate ions the improvement which comprises adding to the hair conditioning composition an effective corrosion-inhibiting amount of a composition comprising the following active ingredients: (a) phosphoric acid, monobutyl ester, disodium salt (disodium butyl phosphate), (b) poly(oxy-1,2-ethanediyl), alpha-phosphono-omega-hydroxy , $C_{13}$—$C_{15}$ alkyl ethers, disodium salts, (c) poly(oxy-1,2-ethanediyl), alpha, alpha-phosphinicobis (omega-hydroxy-, di—$C_{13}$—$C_{15}$ alkyl ethers, sodium salts, and (d) poly(oxy-1,2-ethanediyl), alpha-(butoxyhydroxyphosphinyl)-omega-hydroxy-, $C_{13}$—$C_{15}$ alkyl ethers, sodium salts, whereby the improved hair conditioning composition is substantially non-corrosive to stainless steel and does not exhibit a loss in hair conditioninq properties.

* * * * *

UNITED STATES PATENT AND TRADEMARK OFFICE
CERTIFICATE OF CORRECTION

PATENT NO. : 4,720,382

DATED : January 19, 1988

INVENTOR(S) : Constance E. Erdman; W. Stephen Tait

It is certified that error appears in the above-identified patent and that said Letters Patent is hereby corrected as shown below:

In Column 6, Line 66, the word "conditioninq" should read --conditioning--

In Column 7, Line 4, the word "weiqht" should read --weight--.

In Column 7, Line 8, the words "n butyl" should read --n-butyl--.

In Column 7, Line 22, the word "hydroxy ," should read --hydroxy-,--

In Column 7, Line 24, the word "omega-hydroxy-," should read --omega-hydroxy--.

In Column 7, Line 29, after the word "corrosion" and before the word "inhibiting", insert a dash.

In Column 8, Line 27, the word "conditioninq" should read --conditioning--

In Column 8, Line 34, after the word "alpha-phosphono-omega-hydroxy" insert a dash before the comma.

In Column 8, Line 42, the word "conditioninq" should read --conditioning--

Signed and Sealed this

Fourteenth Day of February, 1989

*Attest:*

DONALD J. QUIGG

*Attesting Officer*  *Commissioner of Patents and Trademarks*